United States Patent [19]

Goldenberg

[11] Patent Number: 5,525,338
[45] Date of Patent: Jun. 11, 1996

[54] DETECTION AND THERAPY OF LESIONS WITH BIOTIN/AVIDIN CONJUGATES

[75] Inventor: David M. Goldenberg, Short Hills, N.J.

[73] Assignee: Immunomedics, Inc., Morris Plains, N.J.

[21] Appl. No.: 933,982

[22] Filed: Aug. 21, 1992

[51] Int. Cl.$^6$ .......................... A61K 38/18; A61K 38/27; A61K 39/385; A61K 39/44

[52] U.S. Cl. ................. 424/178.1; 424/1.41; 424/1.49; 424/85.1; 424/183.1; 424/193.1; 424/94.3; 514/21

[58] Field of Search ................. 424/85.1, 85.2, 424/85.4–85.7, 178.1, 193.1, 94.1, 1.1, 9, 1.49, 1.41, 94.3; 514/21

[56] References Cited

U.S. PATENT DOCUMENTS

| | | | |
|---|---|---|---|
| 4,624,846 | 11/1986 | Goldenberg | 424/1.1 |
| 4,863,713 | 9/1989 | Goodwin et al. | 424/1.1 |
| 4,977,288 | 1/1988 | Kassis et al. | 556/87 |
| 5,283,342 | 2/1994 | Gustavson et al. | |

FOREIGN PATENT DOCUMENTS

WO93/25240  12/1993  WIPO .

OTHER PUBLICATIONS

CA 113(13):113321a and [Sinitsyn et al (1990) Byull. Eksp. Biol. Med 109(6): 567–9.
Fuccillo (1985) Bio Tech 3(6): 494–501.
Yoshikawa et al (1992) J. Pharmacol Expt. Ther. 263(2):897–903.
Paganelli et al (1991) Cancer Res. 51:5960–5966.
Kalofonos et al (1990) J. Nucl. Med. 31:1791–1796.
Hnatowich et al. (1987) J. Nucl. Med 28:1294–1302.
Osband et al (1990) Immunology Today 11(6):193–195.
Harris et al (1993) TIBTECH 11:42–44.
Gould et al (1989) J. Nat'l Cancer Inst. 81(10):775–781.
Waldmann (1991) Science 252:1657–1662.
Hermentin et al (1988) Behring Fast. Mitt. 82:197–215.
Seaver (Aug. 1994) Genetic Engineering News pp. 10 and 21.

*Primary Examiner*—Kay K. A. Kim
*Attorney, Agent, or Firm*—Foley & Lardner

[57] ABSTRACT

Methods are provided for detecting and/or treating lesions in a patient. The methods use a targeting composition comprised of a biotin and targeting protein conjugate or an avidin and targeting protein conjugate; optionally, a clearing composition comprised of avidin, when the targeting composition is a biotin conjugate, or biotin, when the targeting composition is a avidin conjugate; a detection or therapeutic composition comprised of a conjugate of avidin or biotin with a targeting protein and detection or therapeutic agent; and, optionally, another detection or therapeutic composition comprised of avidin or biotin conjugated to a detection or therapeutic agent. Compositions and kits useful in the methods are also provided.

48 Claims, No Drawings

DETECTION AND THERAPY OF LESIONS WITH BIOTIN/AVIDIN CONJUGATES

BACKGROUND OF THE INVENTION

1. Field of the Invention

The present invention relates to improved methods for detecting and treating pathological conditions with a multi-step process using compositions containing biotin and avidin.

2. Description of the Prior Art

Antibodies against different determinants associated with pathological and normal cells, as well as associated with pathogenic microorganisms, have been used for the detection and treatment of a wide variety of pathological conditions, or lesions. The targeting antibody is conjugated to an appropriate detecting or therapeutic agent as described, for example, in Hansen et al., U.S. Pat. Nos. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosure of all of which are incorporated herein by reference.

When detecting a lesion, a high signal-to-background ratio needs to be achieved. Therapy also requires a high absolute accretion of the therapeutic agent in the lesion, as well as a reasonably long duration of uptake and binding. High background levels of non-targeting antibody have long been recognized as a major impediment to high target:background ratios being achieved. To overcome this impediment, various methods have been developed, such as those described in the above-referenced Goldenberg patents.

Still other methods have been developed to increase the target:background ratios of the detection or therapeutic agents, such as pre-targeting and biotin/avidin approaches, as described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; Stickney et al., Cancer Res. 51:6650, 1991; and Yuan et al., Cancer Res. 51:3119, 1991; all incorporated herein in their entirety by reference.

Avidin, found in egg whites, has a very high binding affinity for biotin, which is a B-complex vitamin (Wilcheck et al., Anal. Biochem, 171:1, 1988). Streptavidin, derived from Streptomyces avidinii, is similar to avidin, but has lower non-specific tissue binding, and therefore often is used in place of avidin. Both avidin and streptavidin have a tetravalency for biotin, thus permitting amplification when the former bind to biotin.

In a prior art 2-step procedure, a targeting antibody is conjugated with either avidin or biotin and then is injected into a patient, thus localizing the avidin or biotin at a tumor of interest. Thereafter, either biotin or avidin (depending on which was coupled to the targeting antibody), bearing an imaging isotope, is injected and is localized at the site of the primary antibody by binding to avidin or biotin, respectively.

Timing of the second injection after the first one is very critical. Injecting the radiolabeled avidin or biotin too early will increase the avidin/biotin conjugates in the bloodstream and nontargeted tissues, while injecting very late may decrease the amount targeted to the tumor because of reduced retention of the primary antibody at the tumor.

Paganelli et al. (Int. J. Cancer 2:121, 1988) and Kalofonos et al. (J. Nucl. Med. 31:1791, 1990) demonstrated the feasibility of the above approach (the former used biotinylated antibody; the latter used streptavidin-conjugated antibody for tumor localization). In work reported by Kalofonos et al. (ibid.), 3 of 10 patients showed improved imaging. However, the patients also showed that labeled biotin alone (without antibody pretargeting) could detect tumors in 8 of 10 patients.

Paganelli et al. (J. Nucl. Med. 31:735, 1990 and Cancer Res. 51:5960, 1991) disclose a 3-step approach wherein a biotinylated antibody is administered, followed by cold, i.e., non-labeled and non-conjugated, avidin to clear nontargeted antibody, and then a radiolabeled biotin is given which binds to the avidin retained in the body, presumably where the avidin has complexed to the biotinylated antibody. By this method, Paganelli et al. were able to show, with the exception of the kidneys, high tumor:normal organ ratios. By further examining this 3-step procedure, however, the present inventor has found that cold avidin can reduce the amount of biotin (in the biotinylated antibody) contained in tumor.

Further, many of the above-cited studies have demonstrated that avidin is immunogenic, resulting in antiavidin antibodies which preclude repeated administrations of this agent (and thereby repeated detecting or therapy courses). Many of these 2- and 3-step approaches using biotin or avidin immunoconjugates have shown improved target:background ratios; however, the administration of a clearing agent, such as avidin, after a biotinylated targeting antibody is first given, not only reduces circulating biotinylated antibody, but also reduces the amount of biotinylated antibody in the target lesion.

Therefore, a need exists for better methods and compositions which will allow for higher and more selective targeting and retaining detection and therapeutic agents to and at pathological lesions and for retaining higher amounts of biotin with the original antibody.

OBJECTS OF THE INVENTION

The principal object of the present invention is to provide a method to deliver higher amounts and higher target:nontarget ratios of detection or therapeutic agents.

Another objective of the invention is to provide a method to increase the amount of primary targeting antibody present in a lesion to be detected or treated.

Still another object of the invention is to provide a 3- or multiple-step procedure which targets higher amounts of a detection or therapeutic agent to a lesion.

Yet another object of the invention is to provide a method to restore any cleared primary antibody and/or detection or therapeutic agent from a lesion in a later targeting step.

A further object of the invention is to provide a method to decrease the immunogenicity of the targeting agents.

Yet another object of the invention is to provide a plurality of detection or therapeutic agents within these targeting methods.

Upon further study of the specification and appended claims, further objects and advantages of this invention will become apparent to those skilled in the art.

SUMMARY OF THE INVENTION

In its broadest embodiment, the invention provides a method of detecting and/or treating lesions in a patient. The method comprises the steps of (a) parenterally injecting a subject with a targeting composition comprised of (i) a biotin-protein conjugate or (ii) an avidin-protein conjugate, wherein the protein preferently binds to a marker substance produced or associated with the targeted lesion, and allowing the protein conjugate to preferentially accrete at the targeted lesion; (b) then, optionally, parenterally injecting a clearing composition comprised of (i) avidin, when the targeting composition is a biotin-protein conjugate, or (ii) biotin, when the targeting composition is a avidin-protein conjugate, and allowing the clearing composition to substantially clear the targeting composition from nontargeted sites and to bind to the targeting composition accreted at the targeted lesion; (c) parenterally injecting a detection or therapeutic composition comprised of a conjugate of (i) avidin, protein and detection or therapeutic agent, or (ii) biotin, protein and detection or therapeutic agent, wherein the protein preferentially binds to a marker substance produced by or associated with the targeted lesion and wherein the protein may be the same as the protein of the targeting composition, and allowing the composition to accrete at the targeted lesion; and (d) parenterally injecting, either prior or subsequent to the composition of (c), another detection or therapeutic composition comprised of (i) avidin conjugated to a detection or therapeutic agent, or (ii) biotin conjugated to a detection or therapeutic agent, wherein the detection or therapeutic agent may be the same as the detection on therapeutic agent of step (c), and allowing the conjugate to accrete at the targeted lesion, wherein (i) step (d) is optional if a clearing composition has been administered, (ii) the detection or therapeutic compositions of step (c) and (d) containing avidin are administered as the next step after the administration of a composition containing biotin or of a clearing composition containing avidin, (iii) detection or therapeutic compositions of step (c) and (d) containing biotin are administered as the next step after the administration of a composition containing avidin or of a clearing composition containing biotin.

In variations of the above embodiment, the following compositions are used in each step.

In a three-stage embodiment, first the targeting composition comprised of a biotin-protein conjugate is injected, no clearing composition is administered; then a detection or therapeutic composition comprised of avidin conjugated to a detection or therapeutic agent is injected and then a detection or therapeutic composition comprised of a conjugate of biotin, protein and detection or therapeutic agent is injected.

In a four-step embodiment, first injected is a targeting composition comprised of a biotin-protein conjugate, then injected is a clearing composition comprised of avidin, then injected is a detection or therapeutic composition comprised of avidin conjugated to a detection or therapeutic agent, and lastly injected is a detection or therapeutic composition comprised of a conjugate of biotin, protein and detection or therapeutic agent.

In another four-step embodiment, first injected is a targeting composition comprised of a biotin-protein conjugate, then injected is a clearing composition comprised of avidin, then injected is a detection or therapeutic composition comprised of a conjugate of biotin, protein and detection or therapeutic agent and lastly injected is another detection or therapeutic composition comprised of avidin conjugated to a detection or therapeutic agent.

In another four-step embodiment, first injected is a targeting composition comprised of a biotin-protein conjugate, then injected is a clearing composition comprised of avidin, then injected is a detection or therapeutic composition comprised of biotin conjugated to a detection or therapeutic agent, and lastly injected is a detection or therapeutic composition comprised of a conjugate of avidin, protein and detection or therapeutic agent.

In another three-step embodiment, first injected is a targeting composition comprised of a biotin-protein conjugate, then injected is a clearing composition comprised of avidin, and lastly injected is a detection or therapeutic composition comprised of a conjugate of biotin, protein and detection or therapeutic agent.

In another four-step embodiment, first injected is a targeting composition comprised of a biotin-protein conjugate, then injected is a clearing composition comprised of avidin, then injected is a detection or therapeutic composition comprised of a conjugate of avidin, protein and detection or therapeutic agent, and lastly injected is another detection or therapeutic composition comprised of biotin conjugated to a detection or therapeutic agent.

In another three-step embodiment, first injected is a subject with a targeting composition comprised of an avidin-protein conjugate, then injected is a detection or therapeutic composition comprised of biotin conjugated to a detection or therapeutic agent, and lastly injected is a detection or therapeutic composition comprised of a conjugate of avidin, protein and detection or therapeutic agent.

In another four-step embodiment, first injected is a targeting composition comprised of an avidin-protein conjugate, then injected is a clearing composition comprised of biotin, then injected is a detection or therapeutic composition comprised of biotin conjugated to a detection or therapeutic agent, and lastly injected is a detection or therapeutic composition comprised of a conjugate of avidin, protein and detection or therapeutic agent.

In another four-step embodiment, first injected is an avidin-protein conjugate, then injected is a clearing composition comprised of biotin, then injected is a detection or therapeutic composition comprised of a conjugate of avidin, protein and detection or therapeutic agent, and lastly injected is another detection or therapeutic composition comprised of biotin conjugated to a detection or therapeutic agent.

In another four-step embodiment, first injected is targeting composition comprised of an avidin-protein conjugate, then injected is a clearing composition comprised of biotin, then injected is a detection or therapeutic composition comprised of avidin conjugated to a detection or therapeutic agent, and lastly injected is another detection or therapeutic composition comprised of biotin, protein and detection or therapeutic agent.

In another three-step embodiment, first injected is a targeting composition comprised of an avidin-protein conjugate, then injected is a clearing composition comprised of biotin, and lastly injected is a detection or therapeutic composition comprised of a conjugate of avidin, protein and detection or therapeutic agent.

In another four-step embodiment, first injected is a targeting composition comprised of an avidin-protein conjugate, then injected is a clearing composition comprised of biotin, then injected is a detection or therapeutic composition comprised of a conjugate of biotin, protein and detection or therapeutic agent, and lastly injected is another detection or therapeutic composition comprised of avidin conjugated to a detection or therapeutic agent.

DETAILED DISCUSSION

It has now been found that 3- and 4-step procedures of the present invention are more advantageous for selective detection and therapy of lesions than the methods of the prior art.

In a more preferred embodiment of this invention involving a 3-step approach, a biotinylated targeting antibody or fragment is injected, followed by the application of avidin as a clearing agent. Then, as a third step, instead of administering biotin-conjugated isotope or drug as taught in the prior art, a lesion-targeting antibody or fragment conjugate is administered. The antibody or fragment is either the same as that of the first step or another such targeting antibody or fragment, and is conjugated with biotin and with a detection or therapeutic agent. Using the lesion-targeting antibody or fragment conjugate forms another lattice of complexation of biotin-avidin-biotin, with the added advantage of targeting to the lesion with the antibody or fragment.

The more preferred 4-step methods have two basic approaches. In both, the first step is the injection of a biotinylated antibody or fragment and the second step is the injection of an avidin chase. The third step involves the injection of either avidin conjugated with a detection or therapeutic agent, or alternatively a biotin conjugated with a detection or therapeutic agent. When the third step uses an avidin conjugate, the fourth step is an injection of a biotinylated anti-lesion antibody or fragment conjugated with a detection or therapeutic agent. When the third step involves biotin conjugated with a detection or therapeutic agent, the fourth step requires the injection of an antilesion antibody or fragment conjugated with avidin and with a detection or therapeutic agent.

Each of these 4-step approaches is an improvement, in terms of absolute amount of detection or therapeutic agent delivered and retained at the site of the lesion, as compared to the prior art 2- and 3-step procedures which did not contemplate the use of a biotinylated or avidin-conjugated antibody or fragment bearing additional detection or therapeutic agents for enhancement of the effects as a last step.

Of course, if desired, the sequence can be repeated for additional accumulation of the agents, as needed. Further, the preferred lesion-localizing antibody can be a bispecific or hybrid antibody, whereby at least 2 antibody arms are directed against different epitopes of the same antigen or against different substances associated with the lesion. This is preferred in order to achieve higher levels of accretion and binding in the lesion.

These methods of the present invention provide the following improved results over other sequences reported earlier by others:

1. Increased binding and retention of primary antibody in the lesion;
2. higher lesion:normal organ (including kidney) ratios;
3. increased targeting of detection and therapeutic agents to the lesion; and
4. improved lesion detection or therapy.

The detection/therapeutic agents used in the methods of the present invention can be any or multiples of the following:

A- diagnostic or therapeutic radionuclides (e.g., alpha-, beta-, gamma-, positron-, x-ray- and fluorescence-emitters; electron- and neutron-capturing agents);

B- photoactivated dyes for detection or therapy;

C- cytotoxic agents (e.g., drugs, toxins, hormones, cytokines, hormone antagonists, receptor antagonists);

D- differentiation agents (e.g., vitamins, cytokines, autocrines, certain hormones and drugs).

The methods of the present invention can be used to detect (either by internal procedures or by external imaging) and/or treat lesions, including cancers, infectious diseases, cardiovascular diseases and other pathological conditions.

Internal detection procedures include intraoperative, intravascular or endoscopic, including laparoscopic, techniques, both surgically invasive and non-invasive.

Avidins are a family of proteins functionally defined by their ability to bind biotin with high affinity and specificity.

Avidins are fairly small oligomeric proteins, made up of four identical subunits, each bearing a single binding site for biotin. Avidins can therefore bind up to four moles of biotin per mole of avidin.

Avidins include proteins (a) produced by amphibians, reptiles and avians, which is present in their eggs and known as avidin, and (b) produced by a streptomyces, Streptomyces avidinii, and known as streptavidin. As used herein "avidin" includes all of the above proteins.

Proteins are known which preferentially bind marker substances that are produced by or associated with lesions. For example, antibodies can be used against cancer-associated substances, as well as against any pathological lesion that shows an increased or unique antigenic marker, such as against substances associated with cardiovascular lesions, such as, vascular clots including thrombi and emboli, myocardial infarctions and other organ infarcts, atherosclerotic plaques; inflammatory lesions; and infectious and parasitic agents. Examples of appropriate applications are provided in the above-referenced and incorporated Goldenberg patents and applications.

The cancer states include carcinomas, melanomas, sarcomas, neuroblastomas, leukemias, lymphomas, gliomas and myelomas.

The infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

The protein substances useful in the methods of the present invention include protein, peptide, polypeptide, glycoprotein, lipoprotein, or the like, e.g. hormones, lymphokines, growth factors, albumin, cytokines, enzymes, immune modulators, receptor proteins, antibodies and antibody fragments.

The protein substance of particular interest in the present invention are antibodies and antibody fragments. By "antibodies and antibody fragments" is meant generally immunoglobulins or fragments thereof that specifically bind to antigens to form immune complexes.

The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include F(ab')$_2$, F(ab)$_2$, Fab', Fab Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies and immunoglobulin classes can be used, as can hybrid antibodies.

Multispecific, including bispecific and hybrid, antibodies and antibody fragments are especially preferred in the methods of the present invention for detecting and treating lesions and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,474,893 and 4,479,895, and in Milstein et al., Immunol. Today, 5,299(1984).

Preferred are proteins having a specific immunoreactivity to a marker substance of at least 60% and a cross-reactivity to other antigens or non-targeted substances of less than 35%.

As disclosed above, antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387–398, 1984, showing ready availability. These include monoclonal antibodies (MAbs) against pathogens and their antigens such as the following:

Anti-bacterial Mabs
Streptococcus agalactiae
Legionella pneumophilia
Streptococcus pyogenes
Escherichia coli
Neisseria gonorrhosae
Neisseria meningitidis
Pneumococcus
Hemophilis influenzae B
Treponema pallidum
Lyme disease spirochetes
Pseudomonas aeruginosa
Mycobacterium leprae
Brucella abortus
Mycobacterium tuberculosis
Tetanus toxin
Anti-viral MAbs
HIV-1, -2, -3
Hepatitis A, B, C, D
Rabies virus
Influenza virus
Cytomegalovirus
Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukemia virus*
Mumps virus
Vesicular stomatitis virus
Sindbis virus
Lymphocytic choriomeningitis virus
Wart virus
Blue tongue virus
Sendai virus
Feline leukemia virus*
Reo virus
Polio virus
Simian virus 40*
Mouse mammary tumor virus,
Dengue virus
Rubella virus
*=animal virus
Anti-protozoan MAbs
Plasmodium falciparum
Plasmodium vivax
Toxoplasma gondii
Trypanosoma rangeli
Trypanosoma cruzi
Trypanosoma rhodesiensei
Trypanosoma brucei
Schistosoma mansoni
Schistosoma japanicum
Babesia bovis
Elmeria tenella
Onchocerca volvulus
Leishmania tropica

*Trichinella spiralis*
*Theileria parva*
*Taenia hydatigena*
*Taenia ovis*
*Taenia saginata*
*Echinococcus granulosus*
*Mesocestoides corti*
*Antimycoplasmal MAbs*
*Mycoplasma arthritidis*
*M. hyorhinis*
*M. orale*
*M. arginini*
*Acholeplasma laidlawii*
*M. salivarium*
*M. pneumoniae*

Additional examples of MAbs generated against infectious organisms that have been described in the literature are noted below.

MAbs against the gp120 glycoprotein antigen of human immunodeficiency virus 1 (HIV-1) are known, and certain of such antibodies can have an immunoprotective role in humans. See, e.g., Rossi et al., Proc. Natl. Acad. Sci. USA, 86:8055–8058, 1990. Other MAbs against viral antigens and viral induced antigens are also known. This shows that proper selection of the epitope can distinguish between a therapeutic and non-therapeutic target.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207:71–73, 1980).

Several groups have developed MAbs to T. gondii, the protozoan parasite involved in toxoplasmosis (Kasper et al., J. Immunol. 129:1694–1699, 1982; Id., 130:2407–2412, 1983).

MAbs have been developed against schistosomular surface antigens and have been found to act against schistosomulae in vivo or in vitro (Simpson et al., Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

Trypanosoma cruzi is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are appropriate for use in the present invention.

Proteins useful for detecting and treating cardiovascular lesions include fibrin-specific proteins, for example, fibrinogen, soluble fibrin, antifibrin antibodies and fragments, fragment $E_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins, for example, platelets, antiplatelet antibodies and antibody fragments, anti-activated platelet antibodies, and anti-activated-platelet factors, which have been reviewed by Koblik et al., Semin. Nucl. Med., 19:221–237 1989, all of which is included herein by reference.

Among the radionuclides useful in the methods of the present invention, gamma-emitters, positron-emitters, x-ray emitters and fluorescence-emitters are suitable for localization and/or therapy, while beta- and alpha-emitters and electron- and neutron-capturing agents also can be used for therapy.

Suitable radioisotopes for the methods of the present invention include: Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, phosphorus-33, Yttrium-90, Scandium-47, Samarium-153, Lutetium-177, Rhodium-105, praseodymium-142, praseodymium-143, Terbium-161, Holmium-166, Gold-199, Cobalt-57, Cobalt-58, Chromium-51, Iron-59, Selenium-75, Thallium-201, and Ytterbium-169. Preferably the radioisotope will emit in the 10–5,000 kev range, more preferably 50–1,500 kev, most preferably 50–500 kev.

Isotopes preferred for external imaging include:Iodine123, Iodine-131, Indium-111, Gallium-67, Ruthenium-97, Technetium-99m, Cobalt-57, Cobalt-58, Chromium-51, Iron-59, Selenium-75, Thallium-201, and ytterbium-169.

Isotopes most preferred for internal detection include: Iodine-125, Iodine-123, Iodine-131, Indium-111, Technetium-99m and Gallium-67.

Isotopes preferred for therapeutic use include: Iodine-125, Iodine-131, Rhenium-186, Rhenium-188, Silver-111, Platinum-197, Palladium-109, Copper-67, phosphorus-32, Phosphorus-33, Yttrium-90, Scandium-47, Samarium-153, Lutetium-177, Rhodium-105, Praseodymium-142, Praseodymium-143, Terbium-161, Holmium-166, and Gold-199.

Many drugs and toxins are known which have cytotoxic effects on cells. They are to be found in compendia of drugs and toxins, such as the Merck Index, Goodman and Gilman, and the like, and in the references cited above. Any such drug can be conjugated to or loaded onto the antibody by conventional means well know in the art, and illustrated by analogy to those described above.

The present invention also contemplates dyes used, for example, in photodynamic therapy, conjugated to proteins, biotin or avidin and used in conjunction with appropriate nonionizing radiation, The use of light and porphyrins in methods of the present invention is also contemplated and their use in cancer therapy has been reviewed by van den Bergh (Chemistry in Britain, May 1986, Vol. 22, pp. 430–437), which is incorporated herein in its entirety reference.

Examples of known cytotoxic agents useful in the present invention are listed in Goodman et al., "The Pharmacological Basis of Therapeutics," Sixth Edition, A. G. Gilman et al, eds./Macmillan Publishing Co. New York, 1980. These include taxol, nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used in the methods of the present invention; such drugs are known to these skilled in the art and include puromycin, cycloheximide, and ribonuclease.

Toxins can also be used in the methods of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin.

Toxins in their native form require a minimum of three different biochemical functions to kill cells: a cell binding function, a cytotoxic function, and a function to translocate the toxic activity into the cells.

The modified toxins useful in the present invention differ from native toxins in that the domain providing the cell binding function of the native toxin is nonfunctioning because the domain is missing partially or totally.

Other therapeutic agents useful in the present invention include anti-DNA, anti-RNA, anti-protein and anti-chromatin cytotoxic or antimicrobial agents.

The proteins useful in the methods of the present invention may be labeled or conjugated by a variety of methods known in the art. Many of these methods are disclosed in the above-referenced U.S. Patents and Patent Applications. See also, Rayudu, op. cit.; and Childs et al., *J. Nuc. Med.*, 26, 293(1985). Any conventional method of radiolabeling which is suitable for labeling isotopes for in vivo use will be generally suitable for labeling detection agents according to the present invention.

The avidin/streptavidin, biotin or proteins may be conjugated to therapeutic agents such as drugs, toxins, boron addends, isotopes, fluorescent dyes activated by nonionizing radiation, hormones, autocrines, cytokines, cytoprotective agents, etc., by methods known to those skilled in the art. U.S. Pat. No. 5,057,313, Shih et al, hereby incorporated by reference, teaches one such method.

Other examples are conjugating avidin/streptavidin to (a) iodine by the chloramine-T or Bolton-Hunter procedures, (b) technetium/rhenium by procedures described by Griffiths et al. (Cancer Res. 51:4594, 1991) or Fritzberg et al. (U.S. Pat. No. 5,120,526) and (c) metallic nuclides through bifunctional chelating agents as described by Meares et al. (Br. J. Cancer 62:21, 1990). Additionally avidin/streptavidin/biotin can be bound to dendrimers by procedures described for amino-containing proteins as described by Hnatowich et al. (J. Nucl. Med. 28:1294, 1987).

Biotin can be readily conjugated to proteins (including antibodies and their fragments) via the proteins lysine and cysteine residues, and, if available, their oxidized carbohydrate groups.

The detection or therapeutic agents may be treated by methods, known to those skilled in the art, to permit the agents to be more easily conjugated to biotin, avidin/streptavidin or targeting protein as required.

Loading of drugs onto a carrier, as disclosed in USP 5,057,313, will depend upon the potency of the drug, the efficiency of the antibody targeting and the efficacy of the conjugate once it reaches its target. In most cases, it is desirable to load at least 20, preferably 50 and often 100 or more molecules of a drug on a carrier. The ability to partially or completely detoxify a drug as a conjugate, while it is circulation, can reduce systemic side effects of the drug and permit its use when systemic administration of the unconjugated drug would be unacceptable.

Toxins will often be less heavily loaded than drugs, but it will still be advantageous to load at least 1, preferably 5, and in some cases 10 or more molecules of toxin on a carrier and load at least one carrier chain on the antibody for targeted delivery.

In addition to conjugating radioisotopes to biotin (or to streptavidin) for targeting to tumors (or other lesions), it is possible to conjugate drugs to avidin, for example via a dextran spacer molecule (Schechter et al., Int. J. Cancer 48:167, 1991) for delivery of a cytotoxic agent to tumors in animals.

Methods for treating toxins and, in particular, modified Psuedomonas exotoxins, are disclosed in Batkra et al.,Proc. Natl. Acad. Sci. USA, Vol. 86, pp. 8545–8549, 1989; Seetharam et al., J. Biol. Chem., Vol 266, no. 26, pp. 17376–17381, 1991; and Pastan et al., U.S. Pat. No. 4,892, 827, all incorporated herein by reference.

When conjugating the foregoing quantity of antibody or antibody fragment, the amount of drug or toxin is generally about 0.25 to 5 times, preferably 1–3 times, the amount of antibody or antibody fragment, and the time of reaction is about 10 to 120 minutes, preferably 30–90 minutes.

A physiological solution of the protein conjugate is advantageously metered into sterile vials, e.g., at a unit dosage of about 1.0–500 mg protein conjugate/vial, and the vials are either stoppered, sealed and stored at low temperature, or lyophilized, stoppered, sealed and stored.

Variations and modifications of these formulations will be readily apparent to the ordinary skilled artisan, as a function of the individual needs of the patient or treatment regimen, as well as of variations in the form in which the radioisotopes may be provided or may become available.

The present invention includes methods wherein there is a reduction of the immunogenicity of (a) avidin (b) the therapeutic agent moiety of a conjugate, e.g., the toxin, or (c) the targeting composition, by coupling the immunogenic agent with a carbohydrate polymer or polyol groups. Examples of useful carbohydrates or polyol groups include dextran, polysaccharides, polyethylene glycol (PEG), and the like.

The use of a dextran or another polymer for attachment of the therapeutic agents to avidin, or a dextran or another polymer coupled directly to avidin or streptavidin is desirous to decrease the immunogenicity of the conjugates involving avidin. This then permits repeated applications of avidin alone or as a conjugate, in the treatment courses. If the avidin used in the clearing composition is so coupled then more time may be needed for the clearing composition to fulfill its functions.

In an embodiment of the 3-step improved detection or therapeutic protocol of the present invention, the biotinylated or avidin (streptavidin) lesion-targeting protein can be injected parentally, usually at a protein dose of 0.5 to 50 mg, more preferably within a dose range of 1.0 to 20.0 mg, and still more preferably at 2.0 to 10.0 mg. This can be administered as a single injection or in divided doses. After 1–5 days, more preferably at less than 2 days and even at less than 1 day when the first agent involves a small and rapidly targeting molecule, such as an antibody fragment or subfragment, a dose of unlabeled clearing agent, such as 2.0 to 200.0 mg avidin (more preferably about a ratio of 2.5:1 to 10:1 of avidin to biotinylated protein) when a biotinylated lesion-targeting protein is used as the first agent, is administered parenterally. The clearing agent can be given as a single injection or in divided doses, wherein administering the clearing agent in 2 doses is preferred in certain circumstances. The third step involves injection of the biotinylated (or avidin-conjugated) lesion-targeting protein, as in the first step, but conjugated to a detection or therapeutic agent. The lesion-targeting protein can be identical to that of the first step, or another protein capable of similarly targeting the lesion, such as a second targeting antibody. The third step's reagents can be administered parenterally within 24 hrs of the 2nd step, but also at up to 3 days later. In one detection embodiment, the third step involves 111-In conjugated to biotin attached to a lesion-targeting antibody or antibody fragment. Within 24 hrs of the last injection, more preferably within 4 hrs, planar and single-photon emission computed tomography scans are made with a gamma camera equipped with the appropriate collimator and selecting the appropriate energy windows for the detection isotope being used, such as 173 keV and 247 keV for 111-In. In an embodiment of a 4-step detection or therapy protocol of the present invention, the biotinylated or avidin (streptavidin) lesion-targeting protein can be injected parenterally, usually at a protein dose of 2 to 200 mg, more preferably within a dose range of 5 to 50 mg, more preferably at 2.0 to 10.0 mg. This can be administered as a single or as divided injections. After 1–5 days, more preferably at less than 2 days and even at less than 1 day when the first agent involves a small and rapidly targeting molecule, such as an antibody fragment or subfragment, a dose of unlabeled clearing agent, such as 2.5- to 10-times the dose of the first step's protein (which can be determined also by measuring the amount of first agent's protein circulating in the blood at the time of the second step's injection), is given parenterally. The longer the delay after the first step, the lower the amount (and ratio) of clearing agent given. The clearing agent can be given as a single injection or in divided doses, dividing the administration of the clearing agent into at least 2 doses may be preferable, usually within a short period, such as within 2 hrs. In the third step of one embodiment of the invention, a dose of 2 to 200 mg protein, more preferably 5 to 50 mg, of biotin conjugated with a detection or therapeutic agent, as appropriate, is administered parenterally either as a single dose or in divided doses. A fourth step involves the parenteral administration of avidin (or streptavidin) conjugated to a lesion-targeting agent, which can be the same or different from the first lesion-targeting agent, to which a detection or therapeutic agent, as appropiate, is also attached. In another embodiment, the third step can involve the biotinylated lesion-targeting protein conjugated with a detection or therapeutic agent, as appropriate, and the fourth step the detection or therapeutic agent, as appropriate, conjugated to avidin (or streptavidin). The third step's reagents can be administered within 24 hrs of the 2nd step, but also at up to 7 days or more later, depending upon the targeting time and clearance involving the first two steps. The fourth step can be initiated within 24 hrs of the third step, but also up to 7 days or more later.

Routes of administration include intravenous, intraarterial, intrapleural, intraperitoneal, intrathecal, subcutaneous or by perfusion.

An application of the lesion-specific or lesion-associated protein disclosed hereinabove is for magnetic resonance imaging (mri). In this case, for example, a suitably radiolabeled antibody/fragment or an antibody/fragment bearing a mr image enhancing agent is administered with the intention of obtaining an image of the lesion.

The method of the invention can be practiced either with scintigraphic or magnetic resonance imaging agents. A combination of these imaging agents can also be used, although this requires more complex instrumentation and data processing.

Scintigraphic imaging according to the method of the invention is effected by obtaining a scintigram of the lesion of interest.

The scintigram is normally taken by a gamma imaging camera having one or more windows for detection of energies in the 50–500 keV range. Use of radioisotopes with higher energy, beta, or positron emissions would entail use of imaging cameras with the appropriate detectors, all of which are conventional in the art.

The scintigraphic data can be stored in a computer for later processing.

Methods useful for internal detection and/or treatment of tumors and/or other lesions are disclosed in U.S. Pat. No. 4,782,840; U.S. Pat. No. 4,932,412; and copending U.S. Application 07/879,857, the disclosures of which are incorporated herein by reference. The methods of the present invention can be used to enhance the methods disclosed in these references.

Magnetic resonance imaging (mri) is effected in an analogous manner to scintigraphic imaging except that the imaging agents will contain magnetic resonance (mr) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or T2-dependent imaging techniques, and the composition of the medium in which the agent is dissolved or suspended. These factors, and their relative importance are known in the art. See, e.g., Pykett, *Scientific American*, 246, 78(1982); Runge et al., *Am. J. Radiol.*, 141, 1209(1983).

The mr image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

Preparation of protein, biotin or avidin/streptavidin (molecule) conjugated to a magnetic resonance image enhancing agent can be effected by a variety of methods. In order to load a molecule with a large number of paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. The chelate is normally linked to the molecule by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference.

MRI contrast agents are well known in the art and include, for example, Gadolinium, Iron, Manganese, Rhenium, Europium, Lanthanium, Holmium, and Ferbium.

The mr scans are stored in a computer and the images processed analogously to the scintigraphic data.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Accordingly, these embodiments constitute improved methods and reagents for amplification of protein, especially antibody and antibody fragments, targeting for detecting and therapy of cancer and other pathological conditions.

EXAMPLES

Example 1

Conjugating Antibody or Antibody Fragment to Biotin via Lysine.

An antibody or antibody fragment at a concentration of 1–20 mg/ml in a non-amine containing buffer (e.g., borate, phosphate, etc.), at a suitable concentration (0.05–0.5M), at a slightly elevated pH (7.0–9.5), is mixed with a 1–100 molar excess of the activated ester (succinimide or sulfosuccinimide are preferred) of D-biotin or D-biotin incorporating a spacer arm (such as succinimido-6-[biotinamido] hexanoate). A co-solvent, such as dimethylformamide (DMF) or dimethylsulfoxide (DMSO), may be added to provide a final concentration of up to 20% to facilitate reactant solubility. The reaction solution is stirred for 1–24 hours and kept at a temperature of 4° C. to 37° C. At the end of the reaction period, the modified protein is separated from unbound biotin and other low molecular weight contaminants by size-exclusion chromatography and/or dialysis.

Example 2

Conjugating Antibody or Antibody Fragment to Biotin via Cysteine.

An antibody or antibody fragment at a concentration of 5–20 mg/ml in 0.1–0.5M tris buffer, pH 8.7, is made 0.5–5 mg/ml in 2-mercaptoethanol. The reaction solution is let stand 5–120 min. at a temperature of 4°–37° C. The reduced protein is separated from unreacted thiol by size-exclusion chromatography in 50 mM acetate buffer, pH 4.5. Protein concentration and the number of thiol groups per antibody molecule may be determined at this time. The reduced antibody at a concentration of 1–20 mg/ml in a non-amine containing buffer (e.g., phosphate) at a neutral pH (5.0–7.0) is mixed with a 1–100 molar excess of biotin-maleimide (N-biotinyl-N-[6-maleimido hexanoyl]hydrazide) (Sigma Chem. Co). A co-solvent, e.g., DMF or DMSO, may be added to provide a final concentration of up to 20% to facilitate reactant solubility. The reaction solution is stirred for 1–24 hours at a temperature between 4°–37° C. At the end of the reaction period, the biotinylated protein is separated from unbound biotin and other low molecular weight contaminants by size-exclusion chromatography and/or dialysis.

Example 3

Conjugating Antibody or Antibody Fragments to Biotin via a Carbohydrate.

Antibody at a concentration of 1–20 mg/ml is treated with sodium metaperiodate to a final concentration of 0.1–10 mg/ml in phosphate buffered saline at room temperature for 1–4 hours. Ethylene glycol is added to decompose the remaining periodate. The oxidized IgG is purified from low molecular weight contaminants by size-exclusion chromatography in phosphate buffer. The oxidized antibody (1–20 mg/ml) is reacted with a 1–100 molar excess of biotin-hydrazide (Pierce Chemical Co.) in a non-amine buffer (e.g., phosphate, carbonate, etc.) at neutral pH (5.0–8.0) for 1–48 hours at 4°–37° C. After the optimum time for coupling, the formed hydrazones are reduced by the addition of sodium cyanoborohydride with pH adjustment to >7. The biotinylated antibody is purified by size-exclusion chromatography and/or dialysis.

Example 4

Conjugating Antibody or Antibody Fragments to Biotin via addended Thiol Groups

An antibody or antibody fragment at a concentration of 1–20 mg/ml in a non-amine containing buffer (e.g., borate, carbonate, etc.) at a suitable concentration (0.05–0.5M) and pH (7–10) is mixed with a 1–100 molar excess of 2-iminothiolane hydrochloride (Pierce Chemical Co.). The reaction mixture is made 1–100 mM in EDTA to help prevent disulfide bond formation and held at 4°–37° for from 1–4 hours. The modified protein is purified by size-exclusion chromatography in a neutral to slightly acidic buffer (e.g., acetate, citrate, etc.) pH 5.0–7.0. The purified sulfhydryl substituted antibody (1–20 mg/ml) is mixed with a 1–100 molar excess of biotin maleimide. A co-solvent, e.g., DMF or DMSO, may be added to a final concentration of up to 20% to facilitate reactant solubility. The reaction solution is stirred for 1–24 hours at a temperature between 4°–37° C. At the end of the reaction period, the biotinylated protein is separated from unbound biotin and other low molecular weight contaminants by size-exclusion chromatography and/or dialysis.

Example 5

Conjugating Biotin and Fab' Fragments

An antibody $F(ab')_2$ fragment (obtained by pepsin digestion of the intact antibody) at a concentration of 5–20 mg/ml in phosphate buffer at pH 6–8 is treated with a freshly prepared solution of L-cysteine to give a final cysteine concentration of 1–50 mg/ml. The reaction is allowed to proceed for 1–4 hours at 25°–37° C. At the end of this period, the Fab' fragment is purified from low molecular weight contaminants by size-exclusion chromatography in an acidic buffer (e.g., acetate, etc.) at pH 4.0–6.0. The Fab' fragment is reacted with a 1–100 molar excess of biotinmaleimide at pH 5.0–7.0. A co-solvent, e.g., DMF or DMSO, may be added to a final concentration of up to 20% to facilitate reactant solubility. The reaction is stirred for 1–24 hours at a temperature between 4°–37° C. At the end of the reaction period, the biotinylated antibody fragment is separated from unbound biotin and other low molecular weight contaminants by size-exclusion chromatography and/or dialysis.

Example 6

Determination of Extent of Biotinylation of Proteins

A small amount of biotinylated antibody is heated to 56° in 0.1M phosphate buffer for 10 minutes and enzymatically digested with small volumes of 1% pronase (Sigma Chemical Co.). The digestion is allowed to proceed overnight. The digest is analyzed with a 10 uM solution of avidin saturated with a 100 uM solution of 2-(4'-hydroxyazobenzene)-benzoic acid (HABA) in 0.1M phosphate buffer, pH 7.0. The avidin-HABA solution is titrated with increasing volumes of digested biotinylated antibody as well as a standard biotin solution containing 1–10 mM of biotin. The change in absorbance at 500 nM for each is determined, and the concentration of biotin in the pronase digested biotinylated antibody calculated from reference to the standard curve of the titration of biotin with avidin-HABA.

Example 7

Cancer Imaging with Three-Step Procedure

A patient diagnosed by sigmoidoscopy to have a colonic neoplasm is injected i.v. with 1.0 mg. of a biotinylated MN-14 monoclonal antibody IgG against carcinoembryonic antigen (CEA). Two days later, 5 mg of unlabeled avidin (in two divided doses, 20 min apart) is injected i.v. The next day, 1 mg of biotinylated Mu-9 antibody IgG against colon-specific antigen-p (CSAp) labeled with 111-In (4 mCi) is injected i.v. The patient is scanned with a gamma camera 2 hrs later, and a focus of increased radioactivity is detected in the region of the sigmoid colon, in agreement with the sigmoidoscopy findings.

Example 8

Atherosclerotic Imaging with Three-Step Procedure

A patient with suspected atherosclerotic plaques in various arteries is injected i.v. with 2.0 mg of the biotinylated LL1 monoclonal antibody F(ab')$_2$ against macrophage. One day later, 6 mg of unlabeled avidin (in two divided doses, 15 min apart) is injected i.v. One day later, 1 mg of biotinylated LL1 IgG conjugated with 5 mCi of 111-In is injected i.v., and the patient scanned with a gamma camera 3 hours later. Foci of abnormal radioactivity is found in a tibial artery, the abdominal aorta, and possibly in a right cerebral vessel.

Example 9

Cancer Radioimmunotherapy with a Four-Step Procedure

A patient with several small colonic carcinoma metastases to the liver is injected i.v. with a dose of 10 mg of a first composition comprised of biotinylated MN-14 anti-CEA IgG monoclonal antibody. Two days later, a clearing composition of 25 mg avidin is injected i.v. (in two divided doses, 30 min apart). After another 2 days, a dose of 10 mg of a second composition of biotin having 25 mCi 90-Y is injected i.v. Two weeks later, a second therapy dose of a third composition of 20 mCi 90-Y conjugated to avidin-labeled MN-14 anti-CEA IgG (10 mg) is given i.v. Based upon liver CT scans and plasma CEA titers performed 8 weeks later, significant regression of the liver tumor lesions is observed.

Example 10

Cancer Chemoimmunotherapy with a Four-Step Procedure

A patient with a right lung adenocarcinoma is injected with biotinylated "RS7" anti-lung-cancer IgG i.v. Four days later, avidin is injected i.v. (in two divided doses, 60 minutes apart). After another 2 days, a dose of biotinylated RS7 conjugated with aminodextran-doxorubicin, according to the methods described in the Shih patent (U.S. Pat. No. 4,699,784), is administered i.v. Five days later, a dose of streptavidin conjugated with aminodextran-doxorubicin is administered i.v. Four weeks later, chest CT indicates that the right lung lesion is decreased in size by about 50 percent.

The preceding examples can be repeated with similar success by substituting the generically or specifically described reactants and/or operating conditions of this invention for those used in the preceding examples.

From the foregoing descriptions, one skilled in the art can easily ascertain the essential characteristics of this invention and, without departing from the spirit and scope thereof, can make various changes and modifications of the invention to adapt it to various usages and conditions.

I claim:

1. A method of amplifying the detection or treatment of lesions in a subject, comprising the steps of:
    a) parenterally injecting into said subject a targeting composition comprising a targeting protein that specifically binds to a marker substance produced or associated with said lesion compared to non-lesion sites, covalently conjugated to biotin or avidin, and allowing said targeting composition to preferentially accrete at the targeted lesions;
    b) optionally parenterally injecting into said subject a clearing composition that is capable both of clearing said targeting composition from said non-lesion sites and binding to said targeting composition accreted at said lesion, said clearing composition comprising avidin when said targeting composition contains biotin and comprising biotin when said targeting composition contains avidin;
    c) parenterally injecting into said subject a first detection or therapeutic composition comprising a conjugate composed of covalently linked avidin-targeting protein detection or therapeutic agent, when said targeting composition contains avidin, and composed of covalently linker biotin-targeting protein detection or therapeutic agent when said targeting composition contains biotin, wherein said targeting protein may be the same or different than that of a) above, and allowing said detection or therapeutic composition to preferentially accrete at said lesion;
    d) parenterally injecting into said subject, either prior or subsequent to the composition of c) above, a second detection or therapeutic composition comprising a covalent conjugate of avidin-detection or therapeutic agent when said targeting composition of a) above contains biotin and of biotin-detection, or therapeutic agent when said targeting composition of a) above contains avidin;

wherein step d) above is optional if a clearing composition has been administered.

2. The method of claim 1 for detecting or treating lesions in a patient, the method comprising the steps of:
   (a) parenterally injecting a subject with a targeting composition comprised of
      (i) a biotin-protein conjugate wherein the targeting specifically binds to a marker substance produced or associated with the targeted lesion, and allowing the targeting protein conjugate to preferentially accrete at the targeted lesion;
   (b) then parenterally injecting a first detection or therapeutic composition comprised of
      (i) avidin conjugated to a detection or therapeutic agent and allowing the conjugate to accrete at the targeted lesion; and
   (c) then parenterally injecting a detection or therapeutic composition comprised of a conjugate of
      (i) biotin, targeting protein and second detection or therapeutic agent,
      wherein the targeting protein specifically binds to a marker substance produced by or associated with the targeted lesion and may be the same as the protein of the targeting composition, and allowing the composition to accrete at the targeted lesion.

3. The method of claim 1 for detecting or treating lesions in a patient, the method comprising the steps of:
   (a) parenterally injecting a subject with a targeting composition comprised of
      (i) a biotin-protein conjugate,
      wherein the targeting protein specifically binds to a marker substance produced or associated with the targeted lesion, and allowing the targeting protein conjugate to preferentially accrete at the targeted lesion;
   (b) then parenterally injecting a clearing composition comprised of
      (i) avidin, and allowing the clearing composition to substantially clear the targeting composition from non-targeted sites and to bind to the targeting composition accreted at the targeted lesion;
   (c) then parenterally injecting a first detection or therapeutic composition comprised of
      (i) avidin conjugated to a detection or therapeutic agent and allowing the conjugate to accrete at the targeted lesion; and
   (d) then parenterally injecting a second detection or therapeutic composition comprised of a conjugate of
      (i) biotin, targeting protein and detection or therapeutic agent,
      wherein the targeting protein specifically binds to a marker substance produced by or associated with the targeted lesion and may be the same as the targeting protein of the targeting composition, and allowing the composition to accrete at the targeted lesion.

4. The method of claim 1 for detecting or treating lesions in a patient, the method comprising the steps of:
   (a) parenterally injecting a subject with a targeting composition comprised of
      (i) a biotin-protein conjugate, wherein the targeting protein specifically binds to a marker substance produced or associated with the targeted lesion, and allowing the targeting protein conjugate to preferentially accrete at the targeted lesion;
   (b) then parenterally injecting a clearing composition comprised of
      (i) avidin, and allowing the clearing composition to substantially clear the targeting composition from non-targeted sites and to bind to the targeting composition accreted at the targeted lesion;
   (c) then parenterally injecting a first detection or therapeutic composition comprised of a conjugate of
      (i) biotin, targeting protein and detection or therapeutic agent,
      wherein the targeting protein specifically binds to a marker substance produced by or associated with the targeted lesion and may be the same as the targeting protein of the targeting composition, and allowing the composition to accrete at the targeted lesion; and
   (d) then parenterally injecting second detection or therapeutic composition comprised of
      (i) avidin conjugated to a detection or therapeutic agent, and allowing the conjugate to accrete at the targeted lesion.

5. The method of claim 1 for detecting or treating lesions in a patient, the method comprising the steps of:
   (a) parenterally injecting a subject with a targeting composition comprised of
      (i) a biotin-protein conjugate, wherein the targeting protein specifically binds to a marker substance produced or associated with the targeted lesion, and allowing the targeting protein conjugate to preferentially accrete at the targeted lesion;
   (b) then parenterally injecting a clearing composition comprised of
      (i) avidin, and allowing the clearing composition to substantially clear the targeting composition from non-targeted sites and to bind to the targeting composition accreted at the targeted lesion;
   (c) then parenterally injecting a first detection or therapeutic composition comprised of
      (i) biotin conjugated to a detection or therapeutic agent, and allowing the conjugate to accrete at the targeted lesion; and
   (d) then parenterally injecting a second detection or therapeutic composition comprised of a conjugate of
      (i) avidin, targeting protein and detection or therapeutic agent,
      wherein the targeting protein specifically binds to a marker substance produced by or associated with the targeted lesion and may be the same as the protein of the targeting composition, and allowing the composition to accrete at the targeted lesion.

6. The method of claim 1 for detecting or treating lesions in a patient, the method comprising the steps of:
   (a) parenterally injecting a subject with a targeting composition comprised of
      (i) a biotin-protein conjugate, wherein the targeting protein specifically binds to a marker substance produced or associated with the targeted lesion, and allowing the targeting protein conjugate to preferentially accrete at the targeted lesion;
   (b) then parenterally injecting a clearing composition comprised of
      (i) avidin, and allowing the clearing composition to substantially clear the targeting composition from non-targeted sites and to bind to the targeting composition accreted at the targeted lesion; and
   (c) then parenterally injecting a first detection or therapeutic composition comprised of a conjugate of
      (i) biotin, targeting protein and detection or therapeutic agent, wherein the targeting protein specifically binds to a marker substance produced by or associated with the targeted lesion and may be the same as the targeting protein of the targeting composition, and allowing the composition to accrete at the targeted lesion.

7. The method of claim 1 for detecting or treating lesions in a patient, the method comprising the steps of:
   (a) parenterally injecting a subject with a targeting composition comprised of
      (i) a biotin-protein conjugate, wherein the targeting protein specifically binds to a marker substance produced or associated with the targeted lesion, and allowing the targeting protein conjugate to preferentially accrete at the targeted lesion;
   (b) then parenterally injecting a clearing composition comprised of
      (i) avidin, and allowing the clearing composition to substantially clear the targeting composition from non-targeted sites and to bind to the targeting composition accreted at the targeted lesion;
   (c) then parenterally injecting a detection or therapeutic composition comprised of a conjugate of
      (i) avidin, targeting protein and first detection or therapeutic agent,
      wherein the targeting protein specifically binds to a marker substance produced by or associated with the targeted lesion and may be the same as the targeting protein of the targeting composition, and allowing the composition to accrete at the targeted lesion; and
   (d) then parenterally injecting another detection or therapeutic composition comprised of
      (ii) biotin conjugated to a detection or therapeutic agent, and allowing the conjugate to accrete at the targeted lesion.

8. The method of claim 1 for detecting or treating lesions in a patient, the method comprising the steps of:
   (a) parenterally injecting a subject with a targeting composition comprised of
      (i) an avidin-protein conjugate, wherein the targeting protein specifically binds to a marker substance produced or associated with the targeted lesion, and allowing the targeting protein conjugate to preferentially accrete at the targeted lesion;
   (b) then parenterally injecting a detection or therapeutic composition comprised of
      (i) biotin conjugated to a first detection or therapeutic agent, and allowing the conjugate to accrete at the targeted lesion; and
   (c) then parenterally injecting a detection or therapeutic composition comprised of a conjugate of
      (i) avidin, targeting protein and second detection or therapeutic agent,
      wherein the targeting protein specifically binds to a marker substance produced by or associated with the targeted lesion and may be the same as the targeting protein of the targeting composition, and allowing the composition to accrete at the targeted lesion.

9. The method of claim 1 for detecting or treating lesions in a patient, the method comprising the steps of:
   (a) parenterally injecting a subject with a targeting composition comprised of
      (i) an avidin-protein conjugate, wherein the targeting protein specifically binds to a marker substance produced or associated with the targeted lesion, and allowing the targeting protein conjugate to preferentially accrete at the targeted lesion;
   (b) then parenterally injecting a clearing composition comprised of biotin, and allowing the clearing composition to substantially clear the targeting composition from non-targeted sites and to bind to the targeting composition accreted at the targeted lesion;
   (c) then parenterally injecting a detection or therapeutic composition comprised of
      (i) biotin conjugated to a first detection or therapeutic agent, and allowing the conjugate to accrete at the targeted lesion; and
   (d) then parenterally injecting a detection or therapeutic composition comprised of a conjugate of
      (i) avidin, targeting protein and second detection or therapeutic agent,
      wherein the targeting protein specifically binds to a marker substance produced by or associated with the targeted lesion and may be the same as the targeting protein of the targeting composition, and allowing the composition to accrete at the targeted lesion.

10. The method of claim 1 for detecting or treating lesions in a patient, the method comprising the steps of:
    (a) parenterally injecting a subject with a targeting composition comprised of
       (i) an avidin-protein conjugate, wherein the targeting protein specifically binds to a marker substance produced or associated with the targeted lesion, and allowing the protein conjugate to preferentially accrete at the targeted lesion;
    (b) then parenterally injecting a clearing composition comprised of biotin, and allowing the clearing composition to substantially clear the targeting composition from non-targeted sites and to bind to the targeting composition accreted at the targeted lesion;
    (c) then parenterally injecting a detection or therapeutic composition comprised of a conjugate of
       (i) avidin, targeting protein and first detection or therapeutic agent,
       wherein the targeting protein specifically binds to a marker substance produced by or associated with the targeted lesion and may be the same as the targeting protein of the targeting composition, and allowing the composition to accrete at the targeted lesion; and
    (d) then parenterally injecting a second detection or therapeutic composition comprised of
       (ii) biotin conjugated to a detection or therapeutic agent, and allowing the conjugate to accrete at the targeted lesion.

11. The method of claim 1 for detecting or treating lesions in a patient, the method comprising the steps of:
    (a) parenterally injecting a subject with a targeting composition comprised of
       (i) an avidin-protein conjugate, wherein the targeting protein specifically binds to a marker substance produced or associated with the targeted lesion, and allowing the targeting protein conjugate to preferentially accrete at the targeted lesion;
    (b) then parenterally injecting a clearing composition comprised of biotin, and allowing the clearing composition to substantially clear the targeting composition from non-targeted sites and to bind to the targeting composition accreted at the targeted lesion; (c) then parenterally injecting a first detection or therapeutic composition comprised of
       (i) avidin conjugated to a detection or therapeutic agent and allowing the conjugate to accrete at the targeted lesion; and (d) then parenterally injecting a detection or therapeutic composition comprised of a conjugate of
  (i) biotin, targeting protein and second detection or therapeutic agent,
  wherein the targeting protein specifically binds to a marker substance produced by or associated with the targeted lesion and may be the same as the targeting protein of the targeting composition, and allowing the composition to accrete at the targeted lesion.

12. The method of claim 1 for detecting or treating lesions in a patient, the method comprising the steps of:
  (a) parenterally injecting a subject with a targeting composition comprised of
    (i) an avidin-protein conjugate, wherein the targeting protein specifically binds to a marker substance produced or associated with the targeted lesion, and allowing the targeting protein conjugate to preferentially accrete at the targeted lesion;
  (b) then parenterally injecting a clearing composition comprised of biotin, and allowing the clearing composition to substantially clear the targeting composition from non-targeted sites and to bind to the targeting composition accreted at the targeted lesion; and
  (c) then parenterally injecting a detection or therapeutic composition comprised of a conjugate of
    (i) avidin, targeting protein and detection or therapeutic agent,
  wherein the targeting protein specifically binds to a marker substance produced by or associated with the targeted lesion and may be the same as the targeting protein of the targeting composition, and allowing the composition to accrete at the targeted lesion.

13. The method of claim 1 for detecting or treating lesions in a patient, the method comprising the steps of:
  (a) parenterally injecting a subject with a targeting composition comprised of
    (i) an avidin-protein conjugate, wherein the targeting protein specifically binds to a marker substance produced or associated with the targeted lesion, and allowing the targeting protein conjugate to preferentially accrete at the targeted lesion;
  (b) then parenterally injecting a clearing composition comprised of biotin, and allowing the clearing composition to substantially clear the targeting composition from non-targeted sites and to bind to the targeting composition accreted at the targeted lesion;
  (c) then parenterally injecting a first detection or therapeutic composition comprised of a conjugate of
    (i) biotin, targeting protein and detection or therapeutic agent,
  wherein the targeting protein specifically binds to a marker substance produced by or associated with the targeted lesion and may be the same as the targeting protein of the targeting composition, and allowing the composition to accrete at the targeted lesion; and
  (d) then parenterally injecting a second detection or therapeutic composition comprised of
    (i) avidin conjugated to a detection or therapeutic agent, and allowing the conjugate to accrete at the targeted lesion.

14. The method of claim 1, wherein the lesion is cancerous, cardiovascular, infectious or inflammatory.

15. The method of claim 14, wherein the cardiovascular lesion is a thrombus, embolus, infarct or atherosclerotic plaque.

16. The method of claim 14, wherein the cancerous lesion is a carcinoma, melanoma, sarcoma, neuroblastoma, leukemia, lymphoma, glioma or myeloma.

17. The method of claim 14, wherein the lesion is infectious or inflammatory.

18. The method of claim 1, wherein the targeting protein is a peptide, polypeptide, hormone, lymphokine, growth factor, albumin, cytokine, enzyme, immune modulator, receptor protein, antibody or antibody fragment.

19. The method of claim 1, wherein the protein of the targeting composition and the detection or therapeutic composition are the same.

20. The method of claim 1, wherein the protein of the targeting composition and the detection or therapeutic composition are different.

21. The method of claim 20, wherein the different proteins specifically bind to differing epitopes or molecules of the same marker substance.

22. The method of claim 18, wherein the targeting protein is a monoclonal antibody, or a specific binding fragment thereof.

23. The method of claim 22, wherein the fragment is a Fv, single chain antibody, Fab, Fab', F(ab)$_2$ or F(ab')$_2$.

24. The method of claim 23, wherein the fragment is Fab, Fab', F(ab)$_2$ or F(ab')$_2$.

25. The method of claim 22, wherein the antibody is multispecific.

26. The method of claim 25, wherein the antibody is multispecific to differing epitopes or molecules of a marker substance.

27. The method of claim 18, wherein the targeting protein has a specific immunoreactivity to a marker substance of at least 60% and a cross-reactivity to other antigens or non-target substances of less than 35%.

28. The method of claim 1, wherein the method is for detection of a lesion.

29. The method of claim 28, wherein the method is external imaging or internal detection.

30. The method of claim 29, wherein internal detection is during an operative, intravascular or endoscopic procedure.

31. The method of claim 28, wherein the detection agent is a radionuclide, mri enhancing agent, photoactivated dye or differentiation agent.

32. The method of claim 31, wherein the radionuclide is a gamma-, positron-, x-ray or fluorescence-emitter.

33. The method of claim 31, wherein the differentiation agent is a vitamin, cytokine, autocrine, hormone or drug.

34. The method of claim 31, wherein the radionuclide has an energy between 10 and 5000 keV.

35. The method of claim 34, wherein the radionuclide has an energy between 50 and 500 keV.

36. The method of claim 31, wherein the radionuclide used for imaging is Iodine-123, Iodine-131, Indium-111, Gallium-67, Ruthenium-97, Technetium-99m, Cobalt-57, Cobalt-58, Chromium-51, Iron-59, Selenium-75, Thallium-201, or Ytterbium-169.

37. The method of claim 30, wherein the radionuclide used is Iodine-125, Iodine-123, Iodine-131, Indium-111, Technetium-99m or Gallium-67.

38. The method of claim 31, wherein the mri enhancing agent is a species of Gadolinium, Iron, Manganese, Rhenium, Europium, Lanthanium, Holmium, or Ferbium.

39. The method of claim 1, wherein the method is for treating a lesion.

40. The method of claim 39, wherein the therapeutic agent is an isotope, drug, toxin, fluorescent dye activated by nonionizing radiation, hormone, hormone antagonist, receptor antagonist, autocrine or cytokine.

41. The method of claim 39, wherein the therapeutic agent is an electron- or neutron-capturing agent.

42. The method of claim 40, wherein the isotope is Iodine-125, Iodine-131, Rhenium-186, Rhenium-188, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, or Gold-199.

43. The method of claim 39, wherein the therapeutic agent is an anti-DNA, anti-RNA, anti-protein or anti-chromatin cytoxic or antimicrobial agent.

44. The method of claim 39, wherein the drug is taxol, mechlorethamine, cyclophosphamide, melphalan, uracil mustard, chlorambucil, thiotepa, busulfan, carmustine, lomustine, semustine, streptozocin, dacarbazine, methotrexate, fluorouracil, cytarabine, azaribine, mercaptopurine, thioguanine, vinblastine, vincristine, dactinomycin, daunorubicin, doxorubicin, bleomycin, mithramycin, mitomycin, L-asparaginase, cisplatin, hydroxyurea, procarbazine, mitotane, prednisone, hydroxyprogesterone caproate, medroprogesterone acetate, diethylstilbestrol, ethinyl estradiol, tamoxifen, testosterone propionate and fluoxymesterone.

45. The method of claim 39, wherein the toxin is abrin, alpha toxin, diphtheria toxin, exotoxin, gelonin, pokeweed antiviral protein, ricin, or saporin.

46. The method of claim 39, wherein the drug is puromycin, cycloheximide or ribonuclease.

47. The method of claim 1, wherein the immunogenicity of avidin or of the therapeutic agent conjugate is reduced by coupling the avidin or therapeutic moiety of the conjugate with carbohydrate polymer or polyol groups.

48. The method of claim 1, wherein the immunogenicity of the targeting composition is reduced by coupling with a carbohydrate polymer or polyol groups.

* * * * *